(12) United States Patent
Singh et al.

(10) Patent No.: US 10,626,074 B2
(45) Date of Patent: Apr. 21, 2020

(54) PROCESS FOR PREPARATION OF HALO SUBSTITUTED BENZOIC ACID COMPOUND AND INTERMEDIATES THEREOF

(71) Applicant: SFR LIMITED, Haryana (IN)

(72) Inventors: Amardeep Singh, Haryana (IN); Bhupender Singh, Haryana (IN); Kapil Kumar, Haryana (IN); Rajdeep Anand, Haryana (IN)

(73) Assignee: SRF Limited, Gurgaon (IN)

( * ) Notice: Subject to any disclaimer, the term of this patent is extended or adjusted under 35 U.S.C. 154(b) by 0 days.

(21) Appl. No.: 16/491,026

(22) PCT Filed: Mar. 7, 2018

(86) PCT No.: PCT/IN2018/050127
§ 371 (c)(1),
(2) Date: Sep. 4, 2019

(87) PCT Pub. No.: WO2018/163210
PCT Pub. Date: Sep. 13, 2018

(65) Prior Publication Data
US 2020/0010397 A1    Jan. 9, 2020

(30) Foreign Application Priority Data

Mar. 8, 2017  (IN) .............................. 201711008025
Mar. 8, 2017  (IN) .............................. 201711008026
Mar. 8, 2017  (IN) .............................. 201711008027

(51) Int. Cl.
*C07C 51/15*         (2006.01)
(52) U.S. Cl.
CPC .................... *C07C 51/15* (2013.01)
(58) Field of Classification Search
None
See application file for complete search history.

(56) References Cited

FOREIGN PATENT DOCUMENTS

| JP | 60142950 | * | 7/1985 |
| JP | S60142950 A | | 7/1985 |
| JP | S6130556 A | | 2/1986 |
| JP | S6136244 A | | 2/1986 |
| JP | 61030556 | * | 7/1986 |
| JP | 61036244 | * | 7/1986 |
| JP | 04224535 | * | 8/1992 |
| JP | H04224535 A | | 8/1992 |

OTHER PUBLICATIONS

Machine English Translation of JP 61030556, Kaieda et al., 1986.*
International Search Report and Written Opinion pertaining to Application No. PCT/IN2018/050127 dated Aug. 23, 2018.

* cited by examiner

*Primary Examiner* — Sudhakar Katakam
*Assistant Examiner* — Jennifer C Sawyer
(74) *Attorney, Agent, or Firm* — Dinsmore & Shohl, LLP

(57) ABSTRACT

The present invention provides a process for preparation of halo substituted benzoic acid compound of Formula (1) and intermediates thereof.

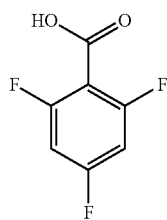

Formula 1

6 Claims, No Drawings

PROCESS FOR PREPARATION OF HALO SUBSTITUTED BENZOIC ACID COMPOUND AND INTERMEDIATES THEREOF

FIELD OF THE INVENTION

The present invention provides a process for preparation of halo substituted benzoic acid compound and intermediates thereof. The halo substituted benzoic acid compounds are very useful raw material for the synthesis of photosensitizers, pharmaceuticals and agro chemicals.

BACKGROUND OF THE INVENTION

The Japan Patent Publication No. S61-030556 provides a process for preparation of 2,4,6-trifluorobenzoic acid by hydrolyzing 3,5-dichloro-2,4,6-trifluorobenzonitrile using aqueous solution of sulfuric acid (40 to 90% by weight) at 140-200° C. followed by dechlorination in the presence of zinc.

The use of sulphuric acid at high temperature leads to the formation of several undesired side products which are required to be removed by purification processes which makes the process unsafe, tedious and uneconomical. 1,3,5-trifluorobenzene can also be used as an intermediate for preparation of 2, 4,6-trifluorobenzoic acid.

The Japan Patent Publication No. H04-224535 provides a process for preparation of 1,3,5-trifluorobenzene by decarboxylating 3,5-dichloro-2,4,6-trifluorobenzoic acid in the presence of organic amine such as tributylamine, trilaurylamine, dimethylaniline or trioctylamine at 150° C. After completion of the reaction, reaction mixture is treated with aqueous hydrochloric acid solution. The organic layer was separated and distilled to obtain 1,3-dichloro-2,4,6-trifluorobenzene. 1,3-dichloro-2,4,6-trifluorobenzene is then dechlorinated using hydrogen in the presence of a palladium-carbon catalyst and hydroxide or carbonate of alkali metals.

The use of hydroxide for dechlorination results in the formation of 1,3-dihydroxy-2,4,6-trifluorobenzene and use of alkali metal carbonates in dechlorination generates carbon dioxide and hydrochloride which results in catalyst deactivation and thus makes the process tedious, unsafe and expensive.

The use of organic amine in decarboxylation requires additional acid-base purification steps which makes the process tedious, uneconomic and unsafe. Thus there is a need to develop a robust, cost effective and safe process for preparation of 2,4,6-trifluorobenzoic acid and intermediates thereof.

SUMMARY OF THE INVENTION

The present invention provides a process for preparation of a compound of Formula 1,

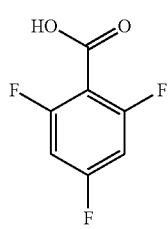

Formula 1 comprising the steps of:

a) contacting a compound of Formula 6

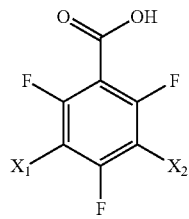

Formula 6 with an inorganic base in the presence of an inorganic sulfate to obtain a compound of Formula 5,

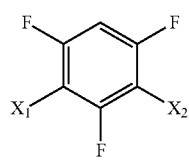

Formula 5 wherein $X_1$ and $X_2$ are independently selected from Cl, Br and I.

b) contacting the compound of Formula 5 with hydrogen in presence of a catalyst and a buffering agent to obtain a compound of Formula 4;

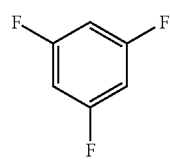

Formula 4 c) converting the compound of Formula 4 to a compound of Formula 3;

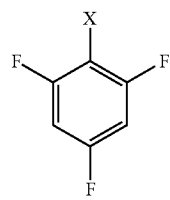

Formula 3 wherein X represents Cl, Br or I;

d) contacting the compound of Formula 3 with magnesium metal to obtain a compound of Formula 2; and

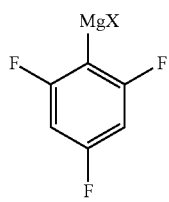

Formula 2 e) contacting the compound of Formula 2 with carbon dioxide to obtain the compound of Formula 1.

OBJECT OF THE INVENTION

The main object of the present invention is to provide a novel, economic and simple process for preparation of a compound of Formula 1 and the intermediates thereof.

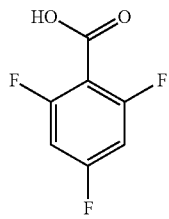

Formula 1

DETAILED DESCRIPTION OF THE INVENTION

In first aspect, the present invention provides a process for preparation of a compound of Formula 1,

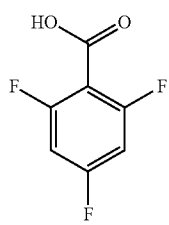

Formula 1 comprising the steps of:
a) contacting a compound of Formula 6,

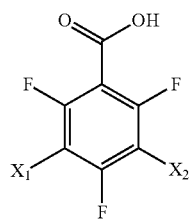

Formula 6 with an inorganic base and an inorganic sulfate to obtain a compound of Formula 5,

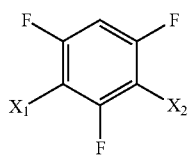

Formula 5 wherein $X_1$ and $X_2$ are independently selected from Cl, Br and I.

b) contacting the compound of Formula 5 with hydrogen in presence of a catalyst and a buffering agent to obtain a compound of Formula 4;

Formula 4 c) converting the compound of Formula 4 to a compound of Formula 3;

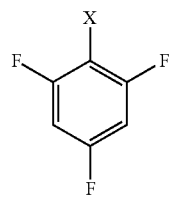

Formula 3 wherein X represents Cl, Br or I;

d) contacting the compound of Formula 3 with magnesium metal to obtain a compound of Formula 2; and

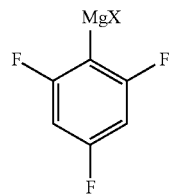

Formula 2 e) contacting the compound of Formula 2 with carbon dioxide to obtain the compound of Formula 1.

In a second aspect, the present invention provides a process for preparation of a compound of Formula 5,

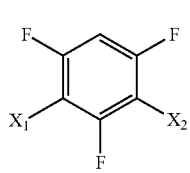

Formula 5 comprising the step of contacting a compound of Formula 6 with an inorganic base and an inorganic sulfate to obtain a compound of Formula 5,

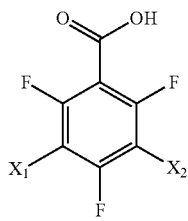

Formula 6 wherein $X_1$ and $X_2$ are independently selected from Cl, Br and I.

In an embodiment of second aspect, the present invention provides a process for preparation of a compound of Formula 5a,

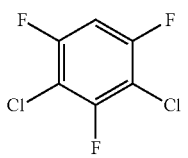

Formula 5a comprising the step of contacting a compound of Formula 6a with an inorganic base and an inorganic sulfate to obtain a compound of Formula 5a,

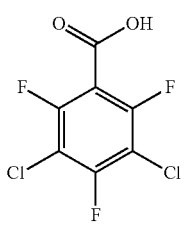

Formula 6a

In a third aspect, the present invention provides a process for preparation of a compound of Formula 4,

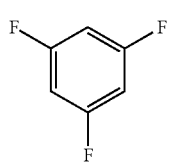

Formula 4 comprising, the step of contacting the compound of Formula 5 with hydrogen in presence of a catalyst and a buffering agent to obtain a compound of Formula 4.

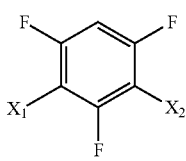

Formula 5 wherein $X_1$ and $X_2$ are independently selected from Cl, Br and I.

In an embodiment of third aspect, the present invention provides a process for preparation of a compound of Formula 4,

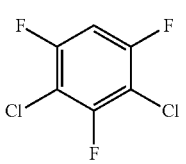

Formula 4 comprising the step of contacting the compound of Formula 5a with hydrogen in presence of a catalyst and a buffering agent to obtain a compound of Formula 4.

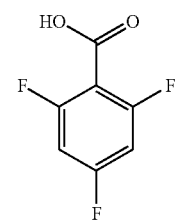

Formula 5a

In a fourth aspect, the present invention provides a process for preparation of a compound of Formula 1,

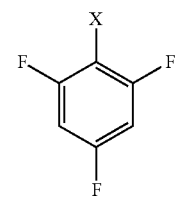

Formula 1 comprising the steps of:
a) contacting the compound of Formula 3

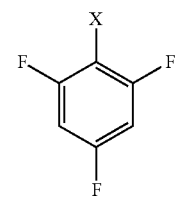

Formula 3 with magnesium metal to obtain a compound of Formula 2; and

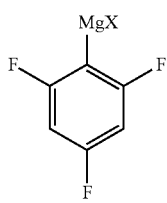

Formula 2 b) contacting the compound of Formula 2 with carbon dioxide to obtain the compound of Formula 1.

In an embodiment of fourth aspect, the present invention provides a process for preparation of a compound of Formula 1,

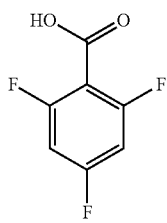

Formula 1 comprising the steps of:

a) contacting the compound of Formula 3a

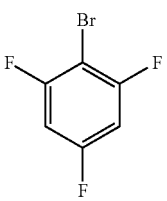

Formula 3a with magnesium metal to obtain a compound of Formula 2a; and

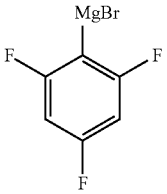

Formula 2a b) contacting the compound of Formula 2a with carbon dioxide to obtain the compound of Formula 1.

The inorganic base used in the present invention is selected from the group consisting of alkali metal hydroxides, alkali earth hydroxides, metal carbonates and metal oxides.

The preferred inorganic base is selected from the group consisting of lithium hydroxide, sodium hydroxide, potassium hydroxide, calcium hydroxide, lithium carbonate, potassium carbonate, sodium carbonate and ammonium carbonate or mixture thereof.

The inorganic sulphates used in the present invention is selected from the group consisting of sodium sulphate, potassium sulphate, ammonium sulphate, calcium sulphate and the like.

The step of converting a compound of Formula 6 to a compound of Formula 5 may be carried out in presence of polar organic solvents.

The polar organic solvents may be selected from diethylene glycol, N,N dimethylformamide, N-methyl-2-pyrrolidone, N,N-dimethylacetamide and dimethyl sulfoxide or the mixture thereof.

The step of converting a compound of Formula 6 to a compound of Formula 5 may be carried out at temperature in the ranging from 100-200° C. for 1 to 8 hours. The catalyst used in the step of conversion of compound of Formula 5 to a compound of Formula 4 is selected from the group consisting of palladium, platinum, nickel, chromium dioxide and Raney nickel supported on alumina or activated carbon.

The buffering agent used in the step of conversion of a compound of Formula 5 to a compound of Formula 4 is selected from the group consisting of metal phosphate and metal acetate or mixture thereof.

The metal phosphate is selected from the group consisting of diammonium phosphate, mono potassium phosphate, dipotassium phosphate, magnesium phosphate, silver phosphate, sodium monofluorophosphate, sodium phosphate, tripotassium phosphate, trisodium phosphate, lead(II) phosphate, lithium iron phosphate, manganese(II) phosphate, potassium titanyl phosphate or mixture thereof.

The metal acetate is selected from the group consisting of sodium acetate, potassium acetate, lithium acetate, calcium acetate and magnesium acetate or mixture thereof.

The step of conversion of a compound of Formula 5 to a compound of Formula 4 may be carried out at suitable pressure between 2 to 15 $Kg/cm^2$ and at a suitable temperature in the range of 90 to 140° C.

The catalyst used in step of conversion of compound of Formula 5 to a compound of Formula 4 may be recovered and reused.

The compound of Formula 1 is isolated by using techniques known in the art for example distillation, filtration, acid-base treatment, evaporation, column chromatography and layer separation or combination thereof.

The isolation of compound of Formula 1 may be carried out by using water or an aqueous acid selected from the group consisting of aqueous hydrochloric acid, aqueous sulphuric acid, aqueous hydrobromic acid, aqueous hydroiodic acid, aqueous perchloric acid, aqueous chloric acid, aqueous phosphoric acid, aqueous acetic acid and aqueous carbonic acid or mixture thereof.

The steps of converting a compound of Formula 3 to a compound of Formula 2 and subsequently to a compound of Formula 1 may be carried out under anhydrous conditions.

The step of converting a compound of Formula 3 to a compound of Formula 2 may be carried out at temperature in the range of 25 to 70° C. for 0.5 hour to 2 hour.

The step of converting a compound of Formula 2 to a compound of Formula 1 may be carried out at temperature in the range of −5 to 10° C. for 1 to 2 hour.

The compound of Formula 1, 4 and 5 so obtained by the process of the present invention has a purity greater than 95%, more preferably greater than 98%, most preferably greater than 99% by gas chromatography.

The compounds of Formula 6 may be prepared by any method known in the prior art, or may be obtained commercially.

EXAMPLES

Example: 1 Preparation of 1,3-dichloro-2,4,6-trifluorobenzene

Diethylene glycol (390 g), calcium hydroxide (20 g) and calcium sulphate hydrate (34 g) were added sequentially in a reaction vessel. The reaction mixture was heated to 120-140° C. 3,5-Dichloro-2,4,6-trifluorobenzoic acid dissolved in diethylene glycol (1170 g) was added to the reaction mixture at 120-140° C. The reaction mass was stirred for additional 1 to 2 hours. The 1,3-dichloro-2,4,6-trifluorobenzene was recovered by distillation at 150-180° C.

Yield: 94%

Purity: 99.5% (by gas chromatography).

Example: 2 Preparation of 1,3,5-trifluorobenzene 1,3-Dichloro-2,4,6-trifluorobenzene (100 g), water (500 g), dipotassium hydrogen phosphate (260 g) and Palladium/carbon (10%; 2 g) were taken in a reaction vessel. Reaction vessel was flushed first with nitrogen and then with hydrogen. The reaction mixture was heated to 140° C. Hydrogen gas was purged continuously into the reaction vessel at 140° C. and 15 kg/centimeter$^2$ pressure. Progress of the reaction was monitored by gas chromatography. After completion of the reaction, reaction mass was cooled to 10-15° C. and excess hydrogen pressure was released. 1,3,5-trifluorobenzene was recovered from the reaction mass. The bottom mass containing Pd/C was filtered, washed with fresh water and recycled in next batch.

Yield: 85%

Purity: 99.6% (gas chromatography).

Example: 3 Preparation of 1-Bromo-2,4,6-trifluorobenzene 1,3,5-trifluorobenzene (65 g) and anhydrous iron chloride (3.25 g) was added sequentially in a reaction vessel. The reaction mixture was heated to 40° C. Bromine (80 g) was added drop wise to the reaction mixture at 35-40° C. in 2-4 hrs. Reaction mass was stirred for additional 1 hr after complete bromine addition. Progress of the reaction was monitored by gas chromatography. After completion of the reaction, reaction mass was cooled to room temperature and quenched with cold water (32 g; 5-25° C.). Layers were separated. Organic was washed with aqueous sodium bisulphite solution (33 g). 1-bromo-2,4,6-trifluorobenzene was recovered under reduced pressure.

Yield (%): 80%

Purity: 98.5% (gas chromatography).

Example: 4 Preparation of 2,4,6-trifluorobenzoic Acid

Tetrahydrofuran (50 ml) and magnesium (5.87 g) were taken into a reaction vessel sequentially. The reaction mixture was heated to 40° C. and 1-bromo-2,4,6-trifluorobenzene solution (47 g in 185 ml THF) was added drop wise at 30 to 35° C. Reaction mass was stirred for 1 hour. Grignard reagent thus formed was cooled to 0° C. to 10° C. and carbon dioxide gas was purged into it. Reaction progress was monitored by HPLC. After completion of the reaction, reaction mass was quenched with 10% aqueous hydrochloric acid (200 g) and extracted with methyl tertiary butyl ether (200 g). The organic layer was concentrated and water was added to it. pH was adjusted using base to dissolve the crude 2, 4,6-trifluorobenzoic acid alkali salt and washed with dichloromethane. The aqueous layer was acidified with conc. hydrochloric acid till complete precipitation and precipitated product was filtered. The 2,4,6-trifluorobenzoic acid was obtained by recrystallizing crude product with water:methanol mixture (80:20).

Yield: 60%

Purity: 99.8% (by HPLC)

We claim:

1. A process for preparation of a compound of formula 1,

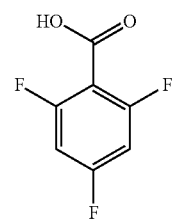

Formula 1 comprising the steps of:
a) contacting a compound of formula 6

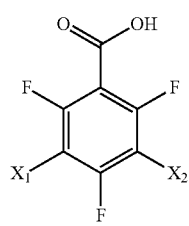

Formula 6 with an inorganic base and an inorganic sulphate to obtain a compound of formula 5,

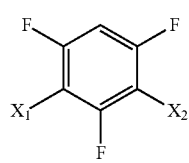

Formula 5 wherein $X_1$ and $X_2$ are independently selected from Cl, Br and I;

contacting the compound of formula 5

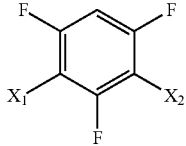

Formula 5 with hydrogen in presence of a catalyst and a buffering agent to obtain a compound of formula 4;

Formula 4 b) converting the compound of formula 4 to formula 3;

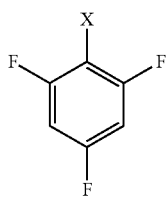

Formula 3 wherein X represents Cl, Br or I;

c) contacting the compound of formula 3 with magnesium metal to obtain a compound of formula 2; and

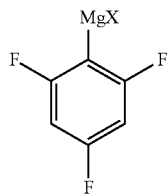

Formula 2 d) contacting the compound of formula 2 with carbon dioxide to obtain the compound of formula 1.

2. The process according to claim 1, wherein the inorganic base is selected from the group consisting of alkali metal hydroxides, alkali earth hydroxides, metal carbonates and metal oxides or a mixture thereof.

3. The process according to claim 2, wherein, the inorganic base is selected from the group consisting of lithium hydroxide, sodium hydroxide, potassium hydroxide, calcium hydroxide, lithium carbonate, potassium carbonate, sodium carbonate and ammonium carbonate, calcium oxide, or a mixture thereof.

4. The process according to claim 1, wherein, the inorganic sulphate is selected from the group consisting of sodium sulphate, potassium sulphate, ammonium sulphate, calcium sulphate, or a mixture thereof.

5. The process according to claim 1, wherein the catalyst is selected from the group consisting of palladium, platinum, nickel, chromium dioxide and Raney nickel supported on alumina or activated carbon.

6. The process according to claim 1, wherein the buffering agent is either a metal phosphate selected from a group consisting of diammonium phosphate, mono potassium phosphate, dipotassium phosphate, magnesium phosphate, silver phosphate, sodium monofluorophosphate, sodium phosphate, tripotassium phosphate, trisodium phosphate, lead(II) phosphate, lithium iron phosphate, manganese(II) phosphate, potassium titanyl phosphate or metal acetates selected from a group consisting of sodium acetate, potassium acetate, lithium acetate, calcium acetate and magnesium acetate or a mixture thereof.

* * * * *